(12) United States Patent
Lehmann et al.

(10) Patent No.: US 7,964,609 B2
(45) Date of Patent: Jun. 21, 2011

(54) USE OF MGLUR5 ANTAGONISTS FOR THE TREATMENT OF GERD

(75) Inventors: Anders Lehmann, Vastra Frolunda (SE); Jan Mattsson, Kullavik (SE); Thomas M. Stormann, Salt Lake City, UT (US)

(73) Assignee: AstraZeneca AB, Sodertalje (SE)

( * ) Notice: Subject to any disclaimer, the term of this patent is extended or adjusted under 35 U.S.C. 154(b) by 66 days.

(21) Appl. No.: 10/517,869

(22) PCT Filed: Jun. 19, 2003

(86) PCT No.: PCT/US03/16223
§ 371 (c)(1),
(2), (4) Date: Oct. 12, 2005

(87) PCT Pub. No.: WO04/000316
PCT Pub. Date: Dec. 31, 2003

(65) Prior Publication Data
US 2006/0128760 A1   Jun. 15, 2006

(30) Foreign Application Priority Data

Jun. 20, 2002   (SE) ..................................... 0201943

(51) Int. Cl.
A61K 31/44 (2006.01)
A61L 31/443 (2006.01)
(52) U.S. Cl. ........................................ 514/277; 514/340
(58) Field of Classification Search ........................ None
See application file for complete search history.

(56) References Cited

U.S. PATENT DOCUMENTS

| 5,036,057 A | 7/1991 | Martin |
| 6,117,908 A | 9/2000 | Andrews et al. |

FOREIGN PATENT DOCUMENTS

| EP | 1 513 525 B1 | 5/2008 |
| WO | WO 98/11885 | 3/1998 |
| WO | WO-9959612 | 11/1999 |
| WO | WO-0051583 | 9/2000 |
| WO | WO-0112627 A | 2/2001 |
| WO | WO-0172291 | 10/2001 |
| WO | WO-02/28837 A1 | 4/2002 |
| WO | 02/068417 A2 | 9/2002 |

OTHER PUBLICATIONS

The Merck Index, 17$^{th}$ edition, (1999), pp. 232-233, 237-238, 2107-2108.*

Gasparini F et al: "2-METHYL-6-(phenylenthynyl)-Pyridine(MPEP), A Potent, Selective andsystemically active MGLU5 Receptor Antagonist" Neuropharmacology, Pergamon press, Oxford, GB, vol. 38 No. 10, Oct. 1999 pp. 1493-1503.
Knöpfel T el al: Metabotropic Glutamate Receptors: Novel targets for drug development Journal of Medicinal Chemisty, American Chemical Society, Washington, US, vol. 38, No. 9 Apr. 28, 1995 pp. 1417-1426.
Chen, C-Y et al., Journal of Physiology (2002), 538.3, pp. 773-786.
Pin, J-P at al., European Journal of Pharmacology (1999), 375, pp. 277-294.
Bräuner-Osborne, H et al. Journal of Medicinal Chemistry (2000), 43, pp. 2609-2645.
Schoepp, D.D, Jane D.E. Monn J.A. Neuropharmacology (1999), 38, pp. 1431-1476.
Holloway & Dent (1990) Gastroenterol. Clin. N. Amer. 19, pp. 517-535.
Martin et al., presentation at the conference Neurogastroenterology & Motility, Madison, Wisconsin, Nov. 14, 2001.
Walker et al., Neuropharmacology, vol. 40, p. 1, (1990) (Abstract).
Spooren et al., Trends Pharmacol. Sci. 22:331 (2001).
Hornby et al., "Receptors and Transmission in the Brain-Gut Axis II. Excitatory amino acid receptors in the brain-gut axis", The Am. J. Physiological Society, 280: G1055-G1060, 2001.
Lehmann et al., "Effects of antagonism of NMDA receptors on transient lower esophageal sphincter relaxations in the dog", European J. of Pharm. 431:253-258, 2001.
O'Leary et al., "Selective mGluR5 antagonists MPEP and SIB-1893 decrease NMDA or glutamate-mediated neuronal toxicity through actions that reflect NMDA receptor antagonism", British J. of Pharm. 131:1429-1437, 2000.
Liu et al., "Agonist-and Reflex-Evoked Internalization of Metabotropic Glutamate Receptor 5 in Enteric Neurons", The J. of Neuroscience, 20(9):3200-3205, May 1, 2000.
Blackshaw et al., "Gastrointestinal pharmacology.-new therapeutic vistas", Current Opinion in Pharm. 1:561-562, 2001.
Kirchgessner, A., "Glutamate in the enteric nervous system", Current Opinion in Pharm. 1:591-596, 2001.
J. T. Greenamyre et al., "Anatomy and physiology of glutamate in the CNS", Neurology 44 (Suppl. 8), Nov., S7-S13, 1994.
D. P. Hirsch et al., "Involvement of Glutamate to Transient Lower Esophageal Sphincter Relaxations in Man", Gastroenterology 120, A-630 (3197), 2001.
J. A. Saugstad et al., "L-2-amino-3-phosphonopropionic acid competitively antagonizes metabotropic glutamate receptors 1α and 5 in *Xenopus* oocytes", Euro. J. of Pharm. 289:395-397, 1995.

(Continued)

*Primary Examiner* — Phyllis G. Spivack
(74) *Attorney, Agent, or Firm* — White & Case LLP

(57) ABSTRACT

The present invention relates to the use of metabotropic glutamate receptor 5 antagonists for the inhibition of transient lower esophageal sphincter relaxations. A further aspect of the invention is directed to the use of metabotropic glutamate receptor 5 antagonists for the treatment of gastroesophageal reflux disease, as well as for the treatment of regurgitation.

9 Claims, No Drawings

OTHER PUBLICATIONS

A. E. Kingston et al., "Pharmacological Analysis of 4-Carboxyphenylglycine Derivatives: Comparison of Effects on mGluR1α and mGluR5a Subtypes", Neuropharm. vol. 34, 8:887-894, 1995.

Wise et al., "Calcium sensing properties of the $GABA_B$ receptor", *Neuropharmacology*, vol. 38 (1999), pp. 1647-1656.

Bordi et al., "Group I metabotropic glutamate receptors: implications for brain diseases", *Progress in Neurobiology* vol. 59, (1999) ,pp. 55-79.

Schmidt et al., "A new phospholipase-C-calcium signaling pathway mediated by cyclic AMP and a Rap GTPase", *Nature Cell Biology*, vol. 3 (2001), pp. 1020-1024; and supplementary information, p. 1.

Spooren et al., "Effects of the prototypical $mGlu_5$ receptor antagonist 2-methyl-6-(phenylethynyl)-pyridine on rotarod, locomotor activity and rotational responses in unilateral 6-OHDA-lesioned rats", *European Journal of Pharmacology*, vol. 406 (2000), pp. 403-410.

Spooren et al., "Novel allosteric antagonists shed light on $mglu_5$ receptors and CNS disorders", *TRENDS in Pharmacological Sciences*, vol. 22, No. 7 (2001), pp. 331-337.

Patentee AstraZeneca's response, dated Jun. 25, 2009, to the Opposition against EP 1 513 525 B1 filed by Addex Pharma S.A. and separately by Novartis AG.

The EPO's preliminary and non-binding opinion dated Oct. 19, 2009 with regard to the Opposition against EP 1 513 525 B1.

Supplemental submission, dated Jul. 28, 2010, by the opponent Novartis AG in its Opposition against EP 1 513 525 B1.

Trilateral Project B3b: Mutual understanding in search and examination: Report on comparative study on biotechnology patent practices: Theme—comparative study on "reach-through claims", EPO, JPO, USPTO, Nov. 5-9, 2001.

K. Sonogashira et al., Tetrahedron Letters. (1975), 50, 4467-4470.

\* cited by examiner

USE OF MGLUR5 ANTAGONISTS FOR THE TREATMENT OF GERD

FIELD OF THE INVENTION

The present invention relates to the use of metabotropic glutamate receptor 5 (mGluR5) antagonists for the inhibition of transient lower esophageal sphincter relaxations. A further aspect of the invention is directed to the use of metabotropic glutamate receptor 5 antagonists for the treatment of gastro-esophageal reflux disease, as well as for the treatment of regurgitation.

BACKGROUND OF THE INVENTION

The metabotropic glutamate receptors (mGluR) are G-protein coupled receptors that are involved in the regulation and activity of many synapses in the central nervous system (CNS). Eight metabotropic glutamate receptor subtypes have been identified and are subdivided into three groups based on sequence similarity. Group I consists of mGluR1 and mGluR5. These receptors activate phospholipase C and increase neuronal excitability. Group II, consisting of mGluR2 and mGluR3 as well as group III, consisting of mGluR4, mGluR6, mGluR7 and mGluR8 are capable of inhibiting adenylyl cyclase activity and reduce synaptic transmission. Several of the receptors also exist in various isoforms, occurring by alternative splicing (Chen, C-Y et al., *Journal of Physiology* (2002), 538.3, pp. 773-786; Pin, J-P et al., *European Journal of Pharmacology* (1999), 375, pp. 277-294; Bräuner-Osborne, H et al. *Journal of Medicinal Chemistry* (2000), 43, pp. 2609-2645; Schoepp, D. D, Jane D. E. Monn J. A. *Neuropharmacology* (1999), 38, pp. 1431-1476).

The lower esophageal sphincter (LES) is prone to relaxing intermittently. As a consequence, fluid from the stomach can pass into the esophagus since the mechanical barrier is temporarily lost at such times, an event hereinafter referred to as "reflux".

Gastro-esophageal reflux disease (GERD) is the most prevalent upper gastrointestinal tract disease. Current pharmacotherapy aims at reducing gastric acid secretion, or at neutralizing acid in the esophagus. The major mechanism behind reflux has been considered to depend on a hypotonic lower esophageal sphincter. However, e.g. Holloway & Dent (1990) *Gastroenterol. Clin. N. Amer.* 19, pp. 517-535, has shown that most reflux episodes occur during transient lower esophageal sphincter relaxations (TLESRs), i.e. relaxations not triggered by swallows. It has also been shown that gastric acid secretion usually is normal in patients with GERD.

According to Blackshaw L. A. et al., presentation at the conference Neurogastroenterology & Motility, Madison, Wis., 14 Nov. 2001, metabotropic glutamate receptors of group II and group III, i.e. mGluR2, mGluR3, mGluR4, mGluR6, mGluR7 and mGluR8 may be involved in selective inhibitory modulation of peripheral mechanosensory endings.

The object of the present invention was to find a new way for the inhibition of transient lower esophageal sphincter relaxations (TLESRs), thereby treating reflux. More particularly the object of the invention was to find a new and improved way of treating gastro-esophageal reflux disease (GERD), as well as a new and improved way for the treatment of regurgitation.

OUTLINE OF THE INVENTION

It has now surprisingly been found that metabotropic glutamate receptor 5 (mGluR5) antagonists are useful for the inhibition of transient lower esophageal sphincter relaxations (TLESRs), and thus for the treatment of gastro-esophageal reflux disease (GERD).

Consequently, the present invention is directed to the use of a metabotropic glutamate receptor 5 antagonist for the manufacture of a medicament for the inhibition of transient lower esophageal sphincter relaxations (TLESRs).

A further aspect of the invention is the use of a metabotropic glutamate receptor 5 antagonist for the manufacture of a medicament for the treatment of reflux.

Still a further aspect of the invention is the use of a metabotropic glutamate receptor 5 antagonist for the manufacture of a medicament for the treatment of gastro-esophageal reflux disease (GERD).

Effective treatment of regurgitation would be an important way of treating, as well as curing lung disease due to aspiration of regurgitated gastric contents, and for managing failure to thrive. Thus, a further aspect of the invention is the use of a metabotropic glutamate receptor 5 antagonist for the manufacture of a medicament for the treatment of regurgitation.

Still a further aspect of the invention is the use of a metabotropic glutamate receptor 5 antagonist for the manufacture of a medicament for the treatment of lung disease.

Another aspect of the invention is the use of a metabotropic glutamate receptor 5 antagonist for the manufacture of a medicament for the management of failure to thrive.

Still a further aspect of the invention is the use of a metabotropic glutamate receptor 5 antagonist for the manufacture of a medicament for the treatment of asthma, such as reflux-related asthma.

Another aspect of the invention is the use of a metabotropic glutamate receptor 5 antagonist for the manufacture of a medicament for the treatment of chronic laryngitis.

A further aspect of the present invention is a method for the inhibition of transient lower esophageal sphincter relaxations (TLESRs), whereby a pharmaceutically and pharmacologically effective amount of a metabotropic glutamate receptor 5 antagonist is administered to a subject in need of such inhibition.

Another aspect of the invention is a method for the treatment of reflux, whereby a pharmaceutically and pharmacologically effective amount of a metabotropic glutamate receptor 5 antagonist is administered to a subject in need of such treatment.

Still a further aspect of the invention is a method for the treatment of gastro-esophageal reflux disease (GERD), whereby a pharmaceutically and pharmacologically effective amount of a metabotropic glutamate receptor 5 antagonist is administered to a subject in need of such treatment.

Yet another aspect of the invention is a method for the treatment of regurgitation, whereby a pharmaceutically and pharmacologically effective amount of a metabotropic glutamate receptor 5 antagonist is administered to a subject in need of such treatment.

Still a further aspect of the invention is a method for the treatment of asthma, such as reflux-related asthma, whereby a pharmaceutically and pharmacologically effective amount of a metabotropic glutamate receptor 5 antagonist is administered to a subject in need of such treatment.

Yet another aspect of the invention is a method for the treatment of chronic laryngitis, whereby a pharmaceutically and pharmacologically effective amount of a metabotropic glutamate receptor 5 antagonist is administered to a subject in need of such treatment. Still a further aspect of the invention is a method for the treatment or inhibition of lung disease, whereby a pharmaceutically and pharmacologically effective amount of a metabotropic glutamate receptor 5 antagonist is administered to a subject in need of such treatment.

Still a further aspect of the invention is a method for the management of failure to thrive, whereby a pharmaceutically and pharmacologically effective amount of a metabotropic glutamate receptor 5 antagonist is administered to a subject in need of such treatment.

For the purpose of this invention, the term "antagonist" should be understood as including full antagonists, inverse agonists, non-competitive antagonists or competitive antagonists, as well as partial antagonists, whereby a "partial antagonist" should be understood as a compound capable of partially, but not fully, in-activating the metabotropic glutamate receptor 5.

The wording "TLESR", transient lower esophageal sphincter relaxations, is herein defined in accordance with Mittal, R. K., Holloway, R. H., Penagini, R., Blackshaw, L. A., Dent, J., 1995; Transient lower esophageal sphincter relaxation. *Gastroenterology* 109, pp. 601-610.

The wording "reflux" is defined as fluid from the stomach being able to pass into the esophagus, since the mechanical barrier is temporarily lost at such times.

The wording "GERD", gastro-esophageal reflux disease, is defined in accordance with van Heerwarden, M. A., Smout A. J. P. M., 2000; Diagnosis of reflux disease. *Baillière's Clin. Gastroenterol.* 14, pp. 759-774.

One example of a compound having antagonistic affinity to metabotropic glutamate receptor 5, thereby being useful in accordance with the invention, is the compound 2-methyl-6-(phenylethynyl)-pyridine (often abbreviated MPEP). MPEP is commercially available from e.g. Tocris, or may be synthesized according to well-known procedures such as disclosed by K. Sonogashira et al. in *Tetrahedron Lett.* (1975), 50, 4467-4470.

A further example of a compound having antagonistic affinity to metabotropic glutamate receptor 5, thereby being useful in accordance with the invention, is the compound 3-[3-(5-fluoropyridin-2-yl)-1,2,4-oxadiazol-5-yl]-5-(methoxymethyl)benzonitrile, having the structural formula:

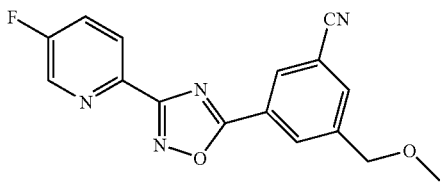

Yet another example of a compound having antagonistic affinity to metabotropic glutamate receptor 5, thereby being useful in accordance with the invention, is the compound 3-fluoro-5-[3-(5-fluoropyridin-2-yl)-1,2,4-oxadiazol-5-yl] benzonitrile, having the structural formula:

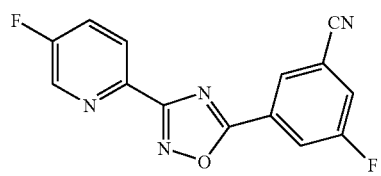

The use of pharmaceutically acceptable salts of metabotropic glutamate receptor 5 antagonists is also within the scope of the present invention. Such salts are for example salts formed with mineral acids such as hydrochloric acid; alkali metal salts such as sodium or potassium salts; or alkaline earth metal salts such as calcium or magnesium salts.

Metabotropic glutamate receptor 5 antagonists having an asymmetric carbon atom are chiral compounds, and depending on the presence of asymmetric atoms, the metabotropic glutamate receptor 5 antagonists may exist in the form of mixtures of isomers, particularly racemates, or in the form of pure isomers such as specific enantiomers. The use of optical isomers of metabotropic glutamate receptor 5 antagonists is also within the scope of the present invention.

Pharmaceutical Formulations

For clinical use, the metabotropic glutamate receptor 5 antagonists are in accordance with the present invention suitably formulated into pharmaceutical formulations for oral administration. Also rectal, parenteral or any other route of administration may be contemplated to the skilled man in the art of formulations. Thus, the metabotropic glutamate receptor 5 antagonists are formulated with at least one pharmaceutically and pharmacologically acceptable carrier or adjuvant. The carrier may be in the form of a solid, semi-solid or liquid diluent.

In the preparation of oral pharmaceutical formulations in accordance with the invention, the metabotropic glutamate receptor 5 antagonist(s) to be formulated is mixed with solid, powdered ingredients such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or compressed into tablets.

Soft gelatine capsules may be prepared with capsules containing a mixture of the active compound or compounds of the invention, vegetable oil, fat, or other suitable vehicle for soft gelatine capsules. Hard gelatine capsules may contain the active compound in combination with solid powdered ingredients such as lactose, saccharose, sorbitol, mannitol, potato starch, corn starch, amylopectin, cellulose derivatives or gelatine.

Dosage units for rectal administration may be prepared (i) in the form of suppositories which contain the active substance(s) mixed with a neutral fat base; (ii) in the form of a gelatine rectal capsule which contains the active substance in a mixture with a vegetable oil, paraffin oil, or other suitable vehicle for gelatine rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions, containing the active compound and the remainder of the formulation consisting of sugar or sugar alcohols, and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent. These solutions may also contain stabilizing ingredients and/or buffering ingredients and are dispensed into unit doses in the form of ampoules or vials.

Solutions for parenteral administration may also be prepared as a dry preparation to be reconstituted with a suitable solvent extemporaneously before use.

In one aspect of the present invention, the metabotropic glutamate receptor 5 antagonists may be administered once or twice daily, depending on the severity of the patient's condition.

A typical daily dose of the metabotropic glutamate receptor 5 antagonists is from 0.1-100 mg per kg body weight of the subject to be treated, but this will depend on various factors such as the route of administration, the age and weight of the patient as well as of severity of the patient's condition.

Biological Evaluation

Screening for Compounds Active Against TLESR

Adult Labrador retrievers of both genders, trained to stand in a Pavlov sling, are used. Mucosa-to-skin esophagostomies are formed and the dogs are allowed to recover completely before any experiments are done.

Motility Measurement

In brief, after fasting for approximately 17 h with free supply of water, a multilumen sleeve/sidehole assembly (Dentsleeve, Adelaide, South Australia) is introduced through the esophagostomy to measure gastric, lower esophageal sphincter (LES) and esophageal pressures. The assembly is perfused with water using a low-compliance manometric perfusion pump (Dentsleeve, Adelaide, South Australia). An air-perfused tube is passed in the oral direction to measure swallows, and an antimony electrode monitored pH, 3 cm above the LES. All signals are amplified and acquired on a personal computer at 10 Hz.

When a baseline measurement free from fasting gastric/LES phase III motor activity has been obtained, placebo (0.9% NaCl) or test compound is administered intravenously (i.v., 0.5 ml/kg) in a foreleg vein. Ten min after i.v. administration, a nutrient meal (10% peptone, 5% D-glucose, 5% Intralipid, pH 3.0) is infused into the stomach through the central lumen of the assembly at 100 ml/min to a final volume of 30 ml/kg. Immediately following the meal, air is insufflated at 40 ml/min. In an alternative model (Barostat model), the infusion of the nutrient meal is followed by air infusion at a rate of 500 ml/min until a intragastric pressure of 10±1 mmHg is obtained. The pressure is then maintained at this level throughout the experiment using the infusion pump for further air infusion or for venting air from the stomach. The experimental time from start of nutrient infusion to end of air insufflation is 45 min. The procedure has been validated as a reliable means of triggering TLESRs.

TLESRs is defined as a decrease in lower esophageal sphincter pressure (with reference to intragastric pressure) at a rate of >1 mmHg/s. The relaxation should not be preceded by a pharyngeal signal ≦2 s before its onset in which case the relaxation is classified as swallow-induced. The pressure difference between the LES and the stomach should be less than 2 mmHg, and the duration of the complete relaxation longer than 1 s.

EXAMPLES

Example 1

2-Methyl-6-(phenylethynyl)-pyridine (MPEP) was prepared according to the procedure described by K. Sonogashira et al. in *Tetrahedron Lett.* (1975), 50, 4467-4470. After purification by column chromatography ($SiO_2$), the hydrochloride salt (the hydrochloride salt of 2-methyl-6-(phenylethynyl)-pyridine is also commercially available from e.g. Tocris) was prepared by introducing HCl(g) to an ice-cooled $Et_2O$-solution of the product. The hydrochloride salt of MPEP was tested on adult Labrador retrievers of both genders in accordance with the test model described above.

Inhibition of the number of TLESRs was calculated with regard to the five preceding control experiments for each dog, and the results as set out in Tables 1.1 and 1.2 below were achieved.

TABLE 1.1

| Standard model | | |
|---|---|---|
| Compound | DOSE [μmol/kg] | % INHIBITION ± SEM (N) |
| MPEP | 1.4 | 30 ± 5(4) |
| MPEP | 4.3 | 57 ± 8(4) |
| MPEP | 8.7 | 59 ± 11(3) |

N = number of dogs tested
SEM = standard error of mean

TABLE 1.2

| Standard model | | |
|---|---|---|
| Compound | DOSE [μmol/kg/h] infusion during 60 min | % INHIBITION ± SEM (N) |
| MPEP | 4 | 32 ± 13(4) |
| MPEP | 6 | 43 ± 3(2) |

N = number of dogs tested
SEM = standard error of mean

Example 2

3-[3-(5-fluoropyridin-2-yl)-1,2,4-oxadiazol-5-yl]-5-(methoxymethyl)benzonitrile was prepared according to the procedure described in WO 02/068417. 3-[3-(5-fluoropyridin-2-yl)-1,2,4-oxadiazol-5-yl]-5-(methoxymethyl)benzonitrile was tested on adult Labrador retrievers of both genders in accordance with the barostat model described above.

TABLE 2.1

| Barostat model | | |
|---|---|---|
| Compound | DOSE [μmol/kg/h] infusion during 55 min | % INHIBITION ± SEM (N) |
| 3-[3-(5-fluoropyridin-2-yl)-1,2,4-oxadiazol-5-yl]-5-(methoxymethyl)benzonitrile | 1.1 | 58 ± 11 (4) |
| 3-[3-(5-fluoropyridin-2-yl)-1,2,4-oxadiazol-5-yl]-5-(methoxymethyl)benzonitrile | 2.2 | 83 ± 17 (2) |

N = number of dogs tested
SEM = standard error of mean

Example 3

3-fluoro-5-[3-(5-fluoropyridin-2-yl)-1,2,4-oxadiazol-5-yl]benzonitrile was prepared according to the procedure described in WO 01/12627. 3-fluoro-5-[3-(5-fluoropyridin-2-yl)-1,2,4-oxadiazol-5-yl]benzonitrile was tested on adult Labrador retrievers of both genders in accordance with the barostat model described above.

TABLE 3.1

| | Barostat model | |
|---|---|---|
| Compound | DOSE [μmol/kg/h] infusion during 60 min | % INHIBITION ± SEM (N) |
| 3-fluoro-5-[3-(5-fluoropyridin-2-yl)-1,2,4-oxadiazol-5-yl]benzonitrile | 1 | 70 ± 4 (3) |

N = number of dogs tested
SEM = standard error of mean

The results shown in the Examples above, support that metabotropic glutamate receptor 5 antagonists are useful for the inhibition of TLESRs, and thus for the treatment of GERD.

The invention claimed is:

1. A method for the inhibition of transient lower esophageal sphincter relaxations (TLESRs) in a patient suffering from gastroesophageal reflux disease (GERD), the method comprising administering a therapeutically effective amount of a compound which is a metabotropic glutamate receptor 5 antagonist, a pharmaceutically acceptable salt of the compound, an optical isomer of the compound or a pharmaceutically acceptable salt of the optical isomer, to the patient.

2. A method for the treatment of gastro-esophageal reflux disease (GERD), the method comprising administering a therapeutically effective amount of a compound which is a metabotropic glutamate receptor 5 antagonist, a pharmaceutically acceptable salt of the compound, an optical isomer of the compound or a pharmaceutically acceptable salt of the optical isomer, to a patient suffering from gastroesophageal reflux disease.

3. A method for the inhibition of reflux of gastric juice in a patient suffering from gastroesophageal reflux disease (GERD), the method comprising administering a therapeutically effective amount of a compound which is a metabotropic glutamate receptor 5 antagonist, a pharmaceutically acceptable salt of the compound, an optical isomer of the compound or a pharmaceutically acceptable salt of the optical isomer, to the patient.

4. A method for the treatment of regurgitation of gastric juice in a patient suffering from gastroesophageal reflux disease (GERD), the method comprising administering a therapeutically effective amount of a compound which is a metabotropic glutamate receptor 5 antagonist, a pharmaceutically acceptable salt of the compound, an optical isomer of the compound or a pharmaceutically acceptable salt of the optical isomer, to the patient.

5. The method according to any one of claims 1-4, wherein the metabotropic glutamate receptor 5 antagonist is 2-methyl-6-(phenylethynyl)-pyridine.

6. The method according to claim 5, wherein the metabotropic glutamate receptor 5 antagonist is the hydrochloride salt of 2-methyl-6-(phenylethynyl)-pyridine.

7. The method according to any one of claims 1-4, wherein the metabotropic glutamate receptor 5 antagonist is 3-[3-(5-fluoropyridin-2-yl)-1,2, oxadiazol-5-yl]-5-(methoxymethyl)benzonitrile.

8. The method according to any one of claims 1-4, wherein the metabotropic glutamate receptor 5 antagonist is 3-fluoro-5-[3-(5-fluoropyridin-2-yl)-1,2,4-oxadiazol-5-yl]benzonitrile.

9. The method according to any one of claims 1-4, wherein the daily dose of the metabotropic glutamate receptor 5 antagonist is from 0.1-100 mg per kg body weight of the subject to be treated.

* * * * *

UNITED STATES PATENT AND TRADEMARK OFFICE
CERTIFICATE OF CORRECTION

| | | |
|---|---|---|
| PATENT NO. | : 7,964,609 B2 | Page 1 of 1 |
| APPLICATION NO. | : 10/517869 | |
| DATED | : June 21, 2011 | |
| INVENTOR(S) | : Lehmann et al. | |

It is certified that error appears in the above-identified patent and that said Letters Patent is hereby corrected as shown below:

<u>Col. 8</u>
Line 23 (claim 7): That portion of the compound printed as "1,2, oxadiazol" should read "1,2,4-oxadiazol".

Signed and Sealed this
Sixteenth Day of August, 2011

David J. Kappos
*Director of the United States Patent and Trademark Office*